US006207960B1

(12) United States Patent
Stern

(10) Patent No.: US 6,207,960 B1
(45) Date of Patent: *Mar. 27, 2001

(54) SYSTEM AND METHODS FOR DETECTION OF LABELED MATERIALS

(75) Inventor: David Stern, Mountain View, CA (US)

(73) Assignee: Affymetrix, Inc, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/295,214

(22) Filed: Apr. 21, 1999

Related U.S. Application Data

(63) Continuation of application No. 08/856,642, filed on May 15, 1997, now Pat. No. 5,981,956.
(60) Provisional application No. 60/017,203, filed on May 16, 1996.

(51) Int. Cl.$^7$ ............................... G01N 21/64; G01J 3/30
(52) U.S. Cl. ..................................... 250/458.1; 250/461.2
(58) Field of Search .............................. 250/458.1, 459.1, 250/206.3, 461.2; 356/344, 317

(56) References Cited

U.S. PATENT DOCUMENTS

| | | |
|---|---|---|
| 3,216,313 | 11/1965 | Chisholm . |
| 3,385,160 | 5/1968 | Dawson et al. . |
| 3,632,212 | 1/1972 | Bernal . |
| 3,798,449 | 3/1974 | Reinheimer et al. . |
| 3,802,966 | 4/1974 | Delekto et al. . |
| 3,984,171 | 10/1976 | Hotchkiss . |
| 4,016,855 | 4/1977 | Mimata . |
| 4,070,111 | 1/1978 | Harrick . |
| 4,176,925 | 12/1979 | Kocher et al. . |
| 4,180,739 | 12/1979 | Abu-Shumays . |
| 4,204,929 | 5/1980 | Bier . |
| 4,342,905 | 8/1982 | Fujii et al. . |
| 4,417,260 | 11/1983 | Kawai et al. . |

(List continued on next page.)

FOREIGN PATENT DOCUMENTS

| | | |
|---|---|---|
| 194 132 | 9/1986 | (EP) . |
| 371 974 | 6/1988 | (EP) . |
| 304 202 | 2/1989 | (EP) . |
| 3-6444 | 1/1991 | (JP) . |
| WO 84/01031 | 3/1984 | (WO) . |
| WO 90/15070 | 12/1990 | (WO) . |
| WO 92/10092 | 6/1992 | (WO) . |
| WO 93/02992 | 2/1993 | (WO) . |
| WO 93/09668 | 5/1993 | (WO) . |
| WO 95/11995 | 5/1995 | (WO) . |

OTHER PUBLICATIONS

Chee et al., "Accessing Genetic Information with High–Density DNA Arrays," *Science*, vol. 274, pp. 610–614 (Oct. 25, 1996).

Lockhart et al., "Expression monitoring by hybridization to high–density oligonucleotide arrays," *Nature Biotechnology*, vol. 14, No. 13, pp. 1675–1680 (Dec. 1996).

Sapolsky et al., "Mapping Genomic Library Clones Using Oligonucleotide Arrays," *Genomics*, vol. 33, Aritcle No. 0219, pp. 445–456 (1996).

(List continued on next page.)

*Primary Examiner*—Constantine Hannaher
*Assistant Examiner*—Albert Gagliardi
(74) *Attorney, Agent, or Firm*—Philip L. McGarrigle; Alan B. Sherr

(57) ABSTRACT

Labeled targets on a support synthesized with polymer sequences at known locations according to the methods disclosed in U.S. Pat. No. 5,143,854 and PCT WO 92/10092 or others, can be detected by exposing marked regions of sample to radiation from a source and detecting the emission therefrom, and repeating the steps of exposition and detection until the sample is completely examined.

33 Claims, 5 Drawing Sheets

Microfiche Appendix Included
(1 Microfiche, 29 Pages)

U.S. PATENT DOCUMENTS

| | | |
|---|---|---|
| 4,448,534 | 5/1984 | Wertz et al. . |
| 4,537,861 | 8/1985 | Elings et al. . |
| 4,579,430 | 4/1986 | Bille . |
| 4,580,895 | 4/1986 | Patel . |
| 4,626,684 | 12/1986 | Landa . |
| 4,772,125 | 9/1988 | Yoshimura et al. . |
| 4,786,170 | 11/1988 | Groebler . |
| 4,810,869 | 3/1989 | Yabe et al. . |
| 4,815,274 | 3/1989 | Piatti . |
| 4,844,617 | 7/1989 | Kelderman et al. . |
| 4,878,971 | 11/1989 | Tsunekawa et al. . |
| 4,963,498 | 10/1990 | Hillman et al. . |
| 5,061,075 | 10/1991 | Alfano et al. . |
| 5,091,652 * | 2/1992 | Mathies et al. ................... 250/458.1 |
| 5,132,524 | 7/1992 | Singh et al. . |
| 5,143,854 | 9/1992 | Pirrung et al. . |
| 5,188,963 | 2/1993 | Stapleton . |
| 5,192,980 | 3/1993 | Dixon et al. . |
| 5,198,871 | 3/1993 | Hill, Jr. et al. . |
| 5,200,051 | 4/1993 | Cozzette et al. . |
| 5,214,531 | 5/1993 | Torii et al. . |
| 5,235,180 | 8/1993 | Montagu . |
| 5,281,516 | 1/1994 | Stapleton et al. . |
| 5,300,779 | 4/1994 | Hillman et al. . |
| 5,304,487 | 4/1994 | Wilding et al. . |
| 5,304,810 | 4/1994 | Amos . |
| 5,310,469 | 5/1994 | Cunningham et al. . |
| 5,320,808 | 6/1994 | Holen et al. . |
| 5,346,672 | 9/1994 | Stapleton et al. . |
| 5,381,224 | 1/1995 | Dixon et al. . |
| 5,382,511 | 1/1995 | Stapleton . |
| 5,384,261 | 1/1995 | Winkler et al. . |
| 5,405,783 | 4/1995 | Pirrung et al. . |
| 5,424,186 | 6/1995 | Fodor et al. . |
| 5,424,841 | 6/1995 | Van Gelder et al. . |
| 5,436,129 | 7/1995 | Stapleton . |
| 5,451,500 | 9/1995 | Stapleton . |
| 5,459,325 | 10/1995 | Hueton et al. . |
| 5,474,796 | 12/1995 | Brennan . |
| 5,486,335 | 1/1996 | Wilding et al. . |
| 5,494,124 | 2/1996 | Dove et al. . |
| 5,498,392 | 3/1996 | Wilding et al. . |
| 5,527,681 | 6/1996 | Holmes . |
| 5,532,873 | 7/1996 | Dixon . |
| 5,571,639 | 11/1996 | Hubbell et al. . |
| 5,572,598 | 11/1996 | Wihl et al. . |
| 5,578,832 | 11/1996 | Trulson et al. . |
| 5,583,342 | 12/1996 | Ichie . |
| 5,585,639 | 12/1996 | Dorsel et al. . |
| 5,631,734 * | 5/1997 | Stern et al. ........................ 356/317 |
| 5,646,411 * | 7/1997 | Kain .................................. 250/458.1 |
| 5,672,880 * | 9/1997 | Kain .................................. 250/458.1 |
| 5,737,121 | 4/1998 | Dixon et al. . |
| 5,760,951 | 6/1998 | Dixon et al. . |
| 5,981,956 * | 11/1999 | Stern ................................. 250/458.1 |

OTHER PUBLICATIONS

Dixon et al., "Confocal scanning beam laser microscope/macroscope: Applications in Fluorescence," Progress in Biomedical Optics, SPIE, Proceedings of Fluorescence Detection IV, vol. 2705, pp. 44–52 (1996).

Alexay et al., "Fluorescence scanner employing a Macro Scanning Objective, " Progress in Biomedical Optics, SPIE, Proceedings of fluorescence Detection IV, vol. 2705, pp. 63–72 (1996).

Pease et al., "Light–generated oligonucleotide arrays for rapid DNA sequence analysis," *Proc. Natl. Acad. Sci, USA,* vol. 91, pp. 5022–5026 (May 1994).

Yamamoto et al., "Features and applications of the laser scanning microscope," *Journal of Modern Optics,* vol. 37, No. 11, pp. 1691–1701 (1990).

Ekins et al., "Multianalyte microspot immunoassay—microanalytical 'compact disk' of the future," *Clin. Chem.,* vol. 37, No. 11, pp. 1955–1967 (Nov. 1991).

Benschop et al., "Confocal compact scanning optical microscope based on compact disk technology," *Chemical Abstracts,* vol. 114, No. 26, p. 114:256643p. (Jul. 1, 1991).

Fodor et al., "Light–Directed, Spatially Addressable Parallel Chemical Synthesis," *Science,* vol. 251, pp. 767–773 (Feb. 15, 1991).

Quesada et al., "High–Sensitivity DNA Detection with a Laser–Excited Confocal Fluorescence Gel Scanner," *BioTechniques,* vol. 10, No. 5, pp. 616–625 (1991).

Yamamoto et al., Features and applications of the laser scanning microscope, *Journal of Modern Optics,* vol. 37, No. 11, pp. 1691–1701 (1990).

Ekins et al., "Development of microspot multianalyte ratiometric immunoassay using dual fluorescent–labelled antibodies," *Analytica Chimica ACTA,* vol. 227, pp. 73–96 (Dec. 1, 1989).

White et al., "An Evaluation of Confocal Versus Convention Imaging of Biological Structures by Fluorescence Light Microscopy," *The Journal of Cell Biology,* vol. 105, No. 1 (Jul. 1987).

Van der voort et al., "Design and Use of a Computer Controlled Confocal Microscope for Biological Applications," *Scanning,* vol. 7, No. 2, pp. 66–78 (1985).

* cited by examiner

SYSTEM AND METHODS FOR DETECTION OF LABELED MATERIALS

CROSS-REFERENCES TO RELATED APPLICATIONS

The present application is a continuation application of U.S. patent application Ser. No. 08/856, 642 filed May 15, 1997, now U.S. Pat. No. 5,981,956 which is a regular application of Provisional U.S. Patent Application Serial No. 60/017,203, filed May 16, 1996, the complete disclosure of which is hereby incorporated herein by reference for all purposes. This application also relates to the commonly assigned, co-pending applications under U.S. patent application Ser. No. 08/301,051, filed Sep. 9, 1994, now U.S. Pat. No. 5,631,734 now U.S. Pat. No. 5,578,832; and U.S. patent application Ser. No. 08/195,889, filed Feb. 10, 1994, the complete disclosures of which are also incorporated herein by reference for all purposes.

COPYRIGHT NOTICE

A portion of the disclosure of this patent document contains material which is subject to copyright protection. The copyright owner has no objection to the facsimile reproduction by anyone of the patent document or the patent disclosure as it appears in Patent and Trademark Office patent file or records, but otherwise reserves all copyright rights whatsoever.

MICROFICHE APPENDIX

Attached hereto is a microfiche Appendix A containing source code listings, which provide a description of the invention suitable for use in a general purpose digital computer system, such as an IBM-compatible personal computer, consists of one (i) slide and 29 frames.

BACKGROUND OF THE INVENTION

The present invention generally relates to the field of imaging. In particular, the present invention provides scanning systems and methods for high speed imaging of a sample containing labeled materials, and particularly for scanning arrays of polymer sequences, e.g., oligonucleotide arrays.

Methods and systems for imaging samples containing labeled markers such as confocal microscopes are commercially available. Confocal microscopes generally employ a pinhole that is confocal with the illuminated spot on the specimen to reject light that is not reflected or emitted from objects in the focal plane. This rejection of out-of-focus light enables the microscope to collect and combine a series of optical slices at different focus positions to generate a two or three dimensional representation of the specimen.

Some scanning microscopes employ radiation direction systems, such as galvanometers that include servo-mounted mirrors, to rapidly scan a laser spot across a substrate. Although these microscopes have relatively high scan rates (e.g., on the order of about 30 lines/second or greater), they generally do not achieve both the resolution and field of view that is necessary for some applications, such as imaging an array of sequenced materials on a substrate. In fact, a galvanometer-based confocal microscope's field of view is generally proportional to its resolution. For example, a typical 40× microscope objective, which has a 0.25 $\mu$m resolution, has a field size of only about 500 $\mu$m. Thus, conventional galvanometer-based confocal microscopes are inadequate for applications requiring both high resolution and a large field of view.

Scanning confocal microscope systems, such as those discussed in U.S. Pat. No. 5,143,854 (Pirrung et al.), PCT WO 92/10092, and U.S. patent application Ser. No. 08/195, 889 (now U.S. Pat. No. 5,631,734), incorporated herein by reference for all purposes, are also known. These scanning systems include an optical train which directs a monochromatic or polychromatic light source to about a 5 micron ($\mu$m) diameter spot at its focal plane. In some cases, a photon counter detects the emission from the device in response to the light. The data collected by the photon counter represents one pixel or data point of the image. Thereafter, the light scans another pixel as a translation stage moves the device to a subsequent position.

As disclosed, these scanning confocal microscope systems provide high resolution by using an appropriate objective lens and large field of view by using appropriate translation stages. These translation stage-based confocal microscopes, however, obtain high resolution and field of view by sacrificing system throughput. As an example, an array of sequenced material using the pioneering fabrication techniques, such as those disclosed in U.S. Pat. No. 5,143, 854 (Pirrung et al.) and U.S. patent application Ser. No. 08/143,312, now abandonded incorporated herein by reference for all purposes, may have a density of about $10^5$ sequences. Assuming that 36 pixels are required for each sequence, the image can take over at least 10 minutes to acquire.

From the above, it is apparent that improved methods and systems for imaging a sample are desired.

SUMMARY OF THE INVENTION

The present invention provides systems, methods and apparatus for detecting marked regions on substrate surfaces. In particular, the present invention provides methods and apparatus for scanning a substrate to obtain an image with high sensitivity and resolution at a high speed. The confocal scanning microscopes of the present invention combine the high scan rate of galvanometer based scanning microscopes with a sufficiently high resolution, sensitivity and a large enough field of view for imaging high density arrays of materials, such as those found in the fields of combinatorial chemistry and genetic analysis.

In one aspect, the present invention provides a system for detecting marked regions on a surface of a substrate, which comprises an excitation radiation source, and focusing optics for focusing the excitation radiation to regions on the surface of the substrate. A radiation direction system is also included for linearly scanning the focused excitation radiation across the surface of the substrate. A detector is positioned for detecting an emission from the substrate surface in response to the excitation radiation, and a data acquisition system records the amount of detected emission as a function of a position on the surface of the substrate from which the emission was detected.

In one embodiment, the focusing optics comprises an objective lens having a ratio of scanning field diameter to focused spot diameter of greater than 2000, preferably greater than 3000 and more preferably greater than 4000. Thus, the microscope is, for example, capable of focusing a laser beam to a spot having a diameter of about 3 microns at any point within a flat field having a length of about 14 mm. In addition, the objective lens has at least a 0.2 numerical aperture, preferably a 0.25 numerical aperture, which provides sufficient sensitivity to detect fluorescently marked regions on the substrate.

The radiation direction system preferably comprises a galvanometer mirror that scans the excitation radiation across the surface of the substrate. The objective lens has an external entrance pupil preferably located at or near the galvanometer mirror's pivot location. The mirror usually oscillates at a frequency of at least 7.5 Hz, preferably at least 20 Hz and more preferably at least 30 Hz. In this manner, the laser spot can usually be scanned across the substrate at velocities of about 5 image lines/second, preferably at least 10 images lines/second, and more preferably at least about 30 image lines/second. This allows the microscope to rapidly scan high density substrates, such as the polymer array substrates disclosed by Pirrung. It should be noted that the mirror may scan unidirectionally (e.g., with a sawtooth wave) or bidirectionally (e.g., with a symmetric triangle wave). In the latter case, the galvanometer frequency would generally be about half of the data acquisition speed in image lines/second. Accordingly, the frequency of the galvanometer in the latter case may be lower than 7.5 Hz in order to scan 5 image lines/second.

In another embodiment, the present invention also provides a system for detecting fluorescent regions on a surface of a substrate, which comprises an excitation radiation source, and first focusing optics for focusing the excitation radiation on the surface of the substrate in a focused spot having a diameter no greater than 10 $\mu$m, preferably less than 5 $\mu$m and more preferably about 3 $\mu$m. An oscillating or reciprocating radiation direction system scans the spot linearly across the surface of the substrate, with a focused travel distance of at least 10 mm and preferably about 14 mm. In one embodiment, an optical train separates fluorescence emitted from the surface of the substrate from the excitation radiation reflected from the surface. An autofocus system may also be included for automatically placing the surface of the substrate in a focal plane of the focusing optics.

The present invention also provides methods of scanning substrates using the above systems. For example, in one aspect, the invention provides a method of scanning a polymer array having a plurality of different polymer sequences, each of the different polymer sequences being immobilized on a surface of a substrate in a different known location, to identify which polymer sequence on the array is bound by a fluorescent target molecule. The method comprises focusing an excitation radiation source upon the surface of the substrate, and scanning the excitation radiation across the surface of the substrate at a speed of at least 5 image lines/second. Fluorescent emissions are collected from the surface of the substrate in response to the excitation radiation. These fluorescent emissions are recorded as a function of a position on the surface of the substrate. The position on the surface indicates the polymer sequence on the array that is bound by the fluorescent target molecule.

A further understanding of the nature and advantages of the inventions herein may be realized by reference to the remaining portions of the specification and the attached drawings.

DESCRIPTION OF THE SPECIFIC EMBODIMENTS

Contents

I. Definitions

II. General

A. Introduction

B. Overview of the Imaging System

Figure 1:
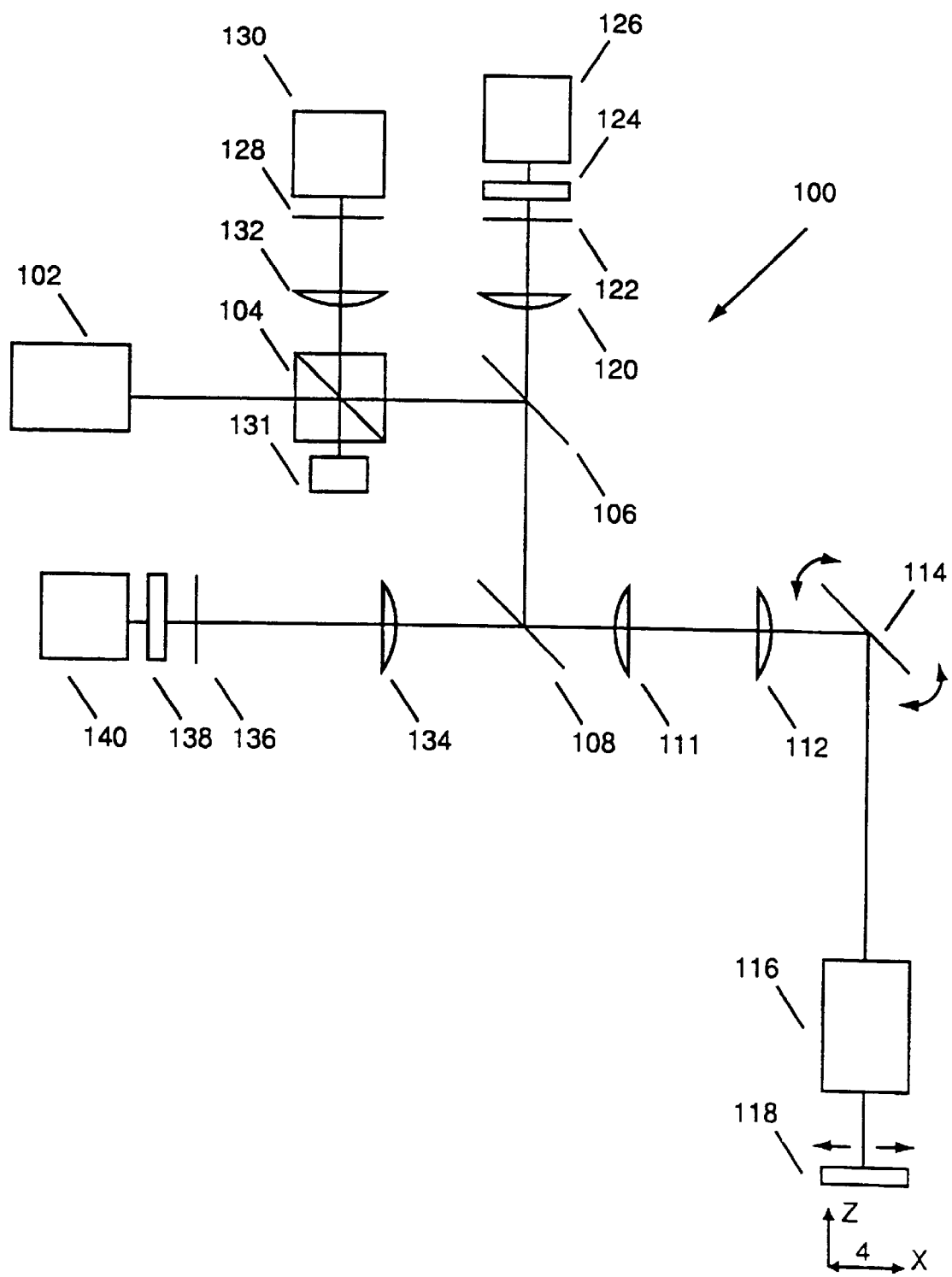
FIG. 1 is a schematic illustration of one embodiment of a scanning system according to the present invention.

III Detailed Description of One Embodiment of the Imaging System

A. Detection Device

B. Data Acquisition

IV. Detailed Description of a Second Embodiment of the Imaging System

I. Definitions

The following terms are intended to have the following general meanings as they are used herein:

1. Complementary: Refers to the topological compatibility or matching together of interacting surfaces of a probe molecule and its target. Thus, the target and its probe can be described as complementary, and furthermore, the contact surface characteristics are complementary to each other.

2. Probe: A probe is a surface-immobilized molecule that is recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

3. Target: A molecule that has an affinity for a given probe. Targets may be naturally-occurring or manmade molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

II. General

A. Introduction

The present invention provides methods and apparatus for scanning a substrate to obtain a highly sensitive and resolved image at a high speed. The invention will have a wide range of uses, particularly, those requiring quantitative study of a microscopic region from within a larger region, such as 2 or 3 $\mu$m$^2$ over 100 mm$^2$. For example, the invention may find application in the field of histology (for studying histochemical stained and immunological fluorescent stained images), or fluorescence in situ hybridization. In one application, the invention herein is used to image an array of probe sequences fabricated on a support.

High resolution scanning systems and methods, whether microscopic or macroscopic, have routinely been used in the electronics industries, e.g., in the semiconductor and microfabrication industries, to scan microfabricated electronics, e.g., microprocessors, microcircuitry, and the like. However, such scanning also has great utility in the field of combinatorial chemistry and genetic analysis. Specifically, high resolution scanning methods and devices can be used in the application of polymer arrays. These polymer arrays are generally made up of a large number of different polymer sequences that are coupled to the surface of a typically planar substrate.

The substrate on which the polymer sequences are formed may be composed from a wide range of material, either biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which a sample is located. The substrate and its surface preferably form a rigid support on which the sample can be formed. The substrate and its surface are also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly) vinylidenedifluoride, polystyrene, polycarbonate, or combinations thereof. Other substrate materials will be readily apparent to those of skill in the art upon review of this disclosure. In a preferred embodiment, the sub-strate is flat glass or silica.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light. The surface may also be provided with reflective "mirror" structures for maximization of emission collected therefrom.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

These arrays are typically prepared in a manner that allows groups of each different polymer sequence to be coupled in a different known location on the substrate surface. The pioneering methods for synthesizing these arrays have been previously described. For example, methods of synthesizing arrays of polymers using light directed synthesis methods are described in U.S. Pat. No. 5,143,854 to Pirrung et al., and U.S. Pat. No. 5,405,783 to Fodor et al., the complete disclosures of which are incorporated herein by reference. Additionally, mechanical methods for synthesizing these arrays are described in, e.g., U.S. Pat. No. 5,384, 261 to Winkler et al., the complete disclosure of which is incorporated herein by reference. Using these pioneering methods, the combination of photolithograpic and fabrication techniques may, for example, enable each probe sequence ("feature") to occupy a very small area ("site") on the support. In some embodiments, this feature site may be as small as a few microns or even a single molecule. For example, about $10^5$ to $10^6$ features may be fabricated in an area of only 163.84 $mm^2$. Such probe arrays may be of the type known as Very Large Scale Immobilized Polymer Synthesis (VLSIPS™). For ease of discussion, the arrays for use with the present invention are described in terms of arrays of different oligonucleotide sequences. However, it should be readily understood that a variety of different polymer array types are equally applicable to the devices of the invention. Furthermore, the scanners of the present invention may also be used in the reflectance mode to scan non-fluorescent surfaces.

In those applications using polymer arrays, such arrays may be prepared having all nucleotide sequences of a given length, composed of the basis set of monomers. For example, an array of oligonucleotides containing all possible sequences of length n which is made up of the basis set of four nucleotides contains up to $4^n$ oligonucleotides on its surface. For an array of 8 mer or 10 mer oligonucleotides, such arrays may include upwards of about 65,536 and 1,048,576 different oligonucleotides, respectively. Generally, where it is desired to produce arrays having all possible polymers of length n, a simple binary masking strategy can be used, as described in U.S. Pat. No. 5,143,854 to Pirrung.

Alternate masking strategies can produce arrays of probes which contain a subset of polymer sequences, i.e., polymers having a given subsequence of monomers, but are systematically substituted at each position with each member of the basis set of monomers. In the context of oligonucleotide probes, these alternate synthesis strategies may be used to lay down or "tile" a range of probes that are complementary to, and span the length of a given known nucleic acid segment. The tiling strategy will also include substitution of one or more individual positions within the sequence of each of the probe groups with each member of the basis set of nucleotides. These positions are termed "interrogation positions." By reading the hybridization pattern of the target nucleic acid, one can determine if and where any mutations lie in the sequence, and also determine what the specific mutation is by identifying which base is contained within the interrogation position. Tiling methods and strategies are discussed in substantial detail in Published PCT Application No. 95/11995, the complete disclosure of which is incorporated herein by reference in its entirety for all purposes.

Tiled arrays may be used for a variety of applications, such as identifying mutations within a known oligonucleotide sequence or "target". Specifically, the probes on the array will have a sub-sequence which is complementary to a known nucleic acid sequence, but wherein at least one position in that sequence has been systematically substituted with the other three nucleotides. See, e.g., U.S. Pat. No. 5,527,681, the complete disclosure of which is incorporated herein by reference.

Generally, the sample nucleic acid for which sequence information is desired is contacted with the array. This "target" sequence is typically labeled with a detectable group such as a fluorescent moiety, i.e., fluorescein or rhodamine. Following hybridization of the target to the array, one can detect the position on the array to which the target sequence binds by scanning the surface of the array for fluorescence.

The surface is typically scanned by directing excitation radiation at the surface to activate the fluorescent labeling group in the target, which in turn emits a fluorescent response radiation. The fluorescent response radiation is detected and assigned to the region from which it originated. By knowing the position from which the fluorescence originates, one can identify the sequence to which the target binds.

Although generally used herein to define separate regions containing differing polymer sequences, the term "feature" generally refers to any element, e.g., region, structure or the like, on the surface of a substrate. Typically, substrates to be scanned using the scanning systems described herein, will have small feature sizes, and consequently, high feature densities on substrate surfaces. For example, individual features will typically have at least one of a length or width dimension that is no greater than 100 μm, and preferably, no greater than 50 μm, and more preferably greater than about 20 μm. Thus, for embodiments employing substrates having a plurality of polymer sequences on their surfaces, each different polymer sequence will typically be substantially contained within a single feature.

The probe arrays will have a wide range of applications. For example, the probe arrays may be designed specifically to detect genetic diseases, either from acquired or inherited mutations in an individual DNA. These include genetic diseases such as cystic fibrosis, diabetes, and muscular dystrophy, as well as acquired diseases such as cancer (P53 gene relevant to some cancers), as disclosed in U.S. patent application Ser. No. 08/143,312, now abandoned already incorporated by reference.

Genetic mutations may be detected by a method known as sequencing by hybridization. In sequencing by hybridization, a solution containing one or more targets to be sequenced (i.e., samples from patients) contacts the probe array. The targets will bind or hybridize with complementary probe sequences. Generally, the targets are labeled with a fluorescent marker, radioactive isotopes, enzymes, or other types of markers. Accordingly, locations at which targets hybridize with complimentary probes can be identified by locating the markers. Based on the locations where hybridization occur, information regarding the target sequences can be extracted. The existence of a mutation may be determined by comparing the target sequence with the wild type.

The interaction between targets and probes can be characterized in terms of kinetics and thermodynamics. As such, it may be necessary to interrogate the array while in contact with a solution of labeled targets. Consequently, the detection system must be extremely selective, with the capacity to discriminate between surface-bound and solution-born targets. Also, in order to perform a quantitative analysis, the high-density volume of the probe sequences requires the system to have the capacity to distinguish between each feature site.

B. Overview of the Imaging System

The devices of the present invention generally employ a scanning device which rapidly sweeps an activation radiation beam or spot across the surface of the substrate. The devices also include focusing optics for focusing the excitation radiation onto the surface of the substrate in a sufficiently small area to provide high resolution of features on the substrate, while simultaneously providing a wide scanning field. An image is obtained by detecting the electromagnetic radiation emitted by the labels on the sample when the labels are illuminated. In one embodiment, fluorescent emissions are gathered by the focusing optics and detected to generate an image of the fluorescence on the substrate surface. In preferred aspects, the devices of the invention further employ confocal detection systems to reduce or eliminate unwanted signals from structures above and below the plane of focus of the excitation radiation, as well as autofocus systems to focus both the activation radiation on the substrate surface and the emitted radiation from the surface. Generally, the excitation radiation and response emission have different wavelengths. Filters having high transmission in the label's emission band and low transmission in the excitation wavelength may be utilized to inhibit the detection of undesirable emission. These generally include emission from out-of-focus planes or scattered excitation illumination as potential sources of background noise.

In operation, the devices of the present invention include one or more sources of excitation radiation. Typically, these source(s) are immobilized or stationary point light sources, e.g., lasers such as argon, helium-neon, diode, dye, titanium sapphire, frequency-doubled diode pumped Nd:YAG and krypton. Typically, the excitation source illuminates the sample with an excitation wavelength that is within the visible spectrum, but other wavelengths (i.e., near ultraviolet or near infrared spectrum) may be used depending on the application (i.e., type of markers and/or sample). In some embodiments, the sample is excited with electromagnetic radiation having a wavelength at or near the absorption maximum of the species of label used. Exciting the label at such a wavelength produces the maximum number of photons emitted. For example, if fluorescein (absorption maximum of 488 nm) is used as a label, an excitation radiation having a wavelength of about 488 nm would induce the strongest emission from the labels.

In instances where a multi-labeling scheme is utilized, a wavelength which approximates the mean of the various candidate labels' absorption maxima may be used. Alternatively, multiple excitations may be performed, each using a wavelength corresponding to the absorption maximum of a specific label. Table I lists examples of various types of fluorophores and their corresponding absorption maxima.

TABLE 1

| Candidate Fluorophores | Absorption Maxima |
|---|---|
| Fluorescein | 488 nm |
| Dichloro-fluorescein | 525 nm |
| Hexachloro-fluorescein | 529 nm |
| Tetramethylrhodamine | 550 nm |
| Rhodamine X | 575 nm |
| Cy3 ™ | 550 nm |
| Cy5 ™ | 650 nm |
| Cy7 ™ | 750 nm |
| IRD40 | 785 nm |

The excitation radiation from the point source is directed at a movable radiation direction system which rapidly scans the excitation radiation beam back and forth across the surface of the substrate. A variety of devices may be employed to generate the sweeping motion of the excitation radiation. For example, resonant scanner or rotating polygons, may be employed to direct the excitation radiation in this sweeping fashion. Generally, however, galvanometer devices are preferred as the scanning system. As used herein, the term "galvanometer" refers to devices that employ a servo motor to oscillate or rotate a mirror over a restricted, predefined range, which is typically less than 90°. This generates a rapidly sweeping or rastering beam reflecting from the galvanometer mirror, which is then directed at and swept across the surface of a substrate that is to be scanned. Typically, an optical train may be employed between the activation source and the galvanometer mirror to assist in directing, focusing or filtering the radiation directed at and reflected from the galvanometer mirror.

The galvanometers employed in the devices and systems of the present invention typically sweep a scanning spot across the substrate surface at an oscillating frequency that is typically greater than about 7.5 Hz, preferably greater than about 20 Hz and more preferably, greater than about 30 Hz. With this frequency, the spot can typically be scanned across the substrate at a velocity of at least about 20 lines/second, preferably in about 5 image lines/second, preferably at least 10 images lines/second, and more preferably at least about 30 image lines/second. It should be noted that the mirror may scan unidirectionally (e.g., with a sawtooth wave) or bidirectionally (e.g., with a symmetric triangle wave). In the latter case, the galvanometer frequency would generally be about half of the data acquisition speed in image lines/second. Accordingly, the frequency of the galvanometer in the latter case may be lower than 7.5 Hz in order to scan 5 image lines/second. The activation radiation is then directed through focusing optics to focus the sweeping beam at the surface of the array which is used to interrogate the target sequence. These same focusing optics also collect emitted fluorescence from the substrate surface for subsequent detection.

The objective lens is preferably selected to provide high resolution, as determined by the focused spot size, while still allowing a wide scanning field. "Focused spot size" is defined by the diameter of the focused activation spot on the surface of the substrate at $1/e^2$ intensity points. "Scanning field" is defined as the length of travel of the focused activation beam or "spot," in one dimension parallel to the direction of travel of the sweeping beam. The confocal system of the present invention generally provides a focused spot size having a diameter no greater than about 10 μm, preferably no greater than about 5 μm, and more preferably about 3 μm. In addition, these systems have a scanning field with a dimension parallel to the direction of the sweep of the activation beam that is usually greater than about 10 mm and more preferably about 14 mm.

For case of discussion, the combined measurement of resolution and effective scanning field are provided as a ratio of the size of the effective field of view of the objective to the size of the focused spot from the scanner. For example, a scanner having a scanning field of 2 mm and a focused spot size of 10 μm would have a ratio of 200 (2 mm/0.010 mm). While a scanner having an effective scanning field of 14 mm with a focused spot size of 3 μm would have a ratio of 4666. In general, the scanning system of the present invention usually has a ratio of size of effective field of view to size of focused spot of at least about 2000, preferably greater than about 3000, and more preferably greater than about 4000. It should be noted that "scanning field" generally refers to the direction in which the galvanometer mirror scans the laser spot across the substrate. The translation stage moves the substrate in the direction orthogonal to the scanned direction, and this direction may be larger than 14 mm.

In one embodiment of the present invention, high fluorescence collection efficiency is achieved by providing an objective lens having a numerical aperture that is at least about 0.2. In particularly preferred aspects, the numerical aperture is at least about 0.25. This translates to an F/number of about F/2.5 to F/2.

In addition to providing smaller spot size while not sacrificing scanning field size, the focusing optics of the scanning system may include a telecentric objective lens. This allows the activation beam to strike the scanning surface at an angle that is substantially normal to that surface, across the entire scanning surface, i.e., regardless of where the input beam is propagating through the lens relative to the lens axis. By "substantially normal" is meant an angle of incidence of approximately 0°, e.g., between 0° and 5°, and preferably from 0° to 2°.

As the activation radiation spot is swept across the surface of the substrate, it activates any fluorescent groups that remain upon the surface, e.g., those that are bound to the surface. The activated groups emit a response radiation or emission which is then collected by the objective lens and directed back through the optical train via the servo mounted mirror. In order to avoid the detrimental effects of reflected excitation radiation upon the detection of the fluorescence, dichroic mirrors or beam splitters may be included in the optical train. These dichroic beam splitters or mirrors are reflective to radiation in the wavelength of the excitation radiation while transmissive to radiation in the wavelength of the response radiation. For example, where an Argon laser is used as the point energy source, it will typically generate activation radiation having a wavelength of about 488 nm. Fluorescence emitted from an activated fluorescein moiety on the other hand will typically have a wavelength between about 515 and 545 nm. As such, dichroic mirrors may be included which transmit light having a wavelength greater than 515 nm while reflecting light of shorter wavelengths. This effectively separates the excitation radiation reflected from the surface of the substrate from the response radiation emitted from the surface of the substrate. Similarly, additional dichroic mirrors may be used to separate signals from label groups having different response radiation wavelengths, thereby allowing simultaneous detection of multiple fluorescent indicators, and thus, simultaneous interrogation of a single array with multiple target sequences. Specifically, a first target sequence may be labeled with a shorter wavelength fluorescent label, e.g., fluorescein, while a second target sequence is labeled with a longer wavelength fluorescent label, e.g., carbocyanin dyes such as CY3 which emit response radiation in the range of 550 to 600 nm. The response radiation from each of these targets may be separated and individually detected through the inclusion of additional dichroic beam splitters and detectors.

Following separation of the response radiation from the reflected excitation radiation, the response radiation or fluorescence is then directed at a detector, e.g., a photomultiplier tube, to measure the level of response radiation and record that level as a function of the position on the substrate from which that radiation originated. Typically, the response radiation is focused upon the detector through a spatial filter such as a confocal pinhole. Such spatial filters reduce or eliminate unwanted signals from structures above and below the plane of focus of the excitation radiation. Additionally, the device may incorporate a bandpass filter between the dichroic mirror and the detector to further restrict the wavelength of radiation that is delivered to the detector.

As noted above, the reflected excitation radiation may generally be used in an autofocusing system in the devices described herein. In particular, the reflected excitation radiation may also be directed at a detector, e.g., a photodiode, that is preferably located behind another spatial filter, i.e., a confocal pinhole.

The substrate surface may be moved closer to and further from the objective lens using, e.g., a translation stage upon which the substrate is mounted. As the substrate is moved out of focus, the amount of reflected excitation radiation contacting the photodiode will be reduced. As the substrate is brought back into focus, this amount will increase, reaching a maximal value when the substrate is in focus. Control for the autofocus system is generally supplied by an appropriately programmed computer, which moves the translation stage in response to the input from the photodiode, until a maximum is reached. Generally, this computer is the same computer which receives, compiles and stores the input from the fluorescence detector or photomultiplier tube, to produce an output of fluorescence as a function of position on the array, typically in the form of a numerical representation or a scan image. Examples of autofocus confocal systems for use in fluorescent scanning devices are generally described in commonly assigned, co-pending U.S. patent application Ser. No. 08/195,889, filed Feb. 10, 1994, now U.S. Pat. No. 5,631,734 the complete disclosure of which is incorporated herein by reference for all purposes. These autofocus systems generally permit the focusing of light reflected from a weakly reflecting surface, e.g., the wet side of a glass substrate, even in the vicinity of a strongly reflecting surface, e.g., the dry side of a glass substrate, as well as being capable of focusing on a featureless surface, e.g., smooth glass.

III. Detailed Description of One Embodiment of the Imaging System.

A. Detection Device

FIG. 1 is an optical block diagram illustrating the imaging system 100 according to the present invention. Typically, imaging system 100 is used to obtain images of oligonucleotide probe arrays to which fluorescently labeled DNA or RNA is bound. It might also be used for other applications, such as wafer or mask inspection, or for imaging of polypeptide or other polymer arrays, electrophoresis gels, or biological specimens. As shown in FIG. 1, a beam of excitation radiation, e.g., 488 nm light, from a laser 102 is partially reflected and partially transmitted by a beamsplitter 104. The reflected portion of the beam impinges upon a photodetector 131 (optional), which is typically a photodiode used as a laser power monitor. The portion of the beam that is transmitted through beamsplitter 104 is reflected by dichroic beamsplitters 106 and 108 and transmitted through lenses 111 and 112, which provide a telescope to expand the beam emitted by laser 102 and to demagnify the collimated fluorescence obtained from the surface of the substrate. In an exemplary embodiment, lens 111 has a focal length of 20 mm and lens 112 has a focal length of 80 mm. Other focal lengths and focal length ratios can be used, but system performance (confocality, resolution, etc.) may be affected. The expanded laser beam is reflected by mirror 114 and focused by lens 116, which is described in more detail below.

Mirror 114, which typically is an 18 mm×28 mm octagon or ellipse, is a galvanometer mirror that oscillates (i.e., scans) at a rate of typically several Hertz or several tens of Hertz. In preferred aspects, the galvanometer mirror oscillates at frequencies greater than 7.5 Hz, preferably about 20 Hz and more preferably about 30 Hz. A resonant scanner or rotating polygonal mirror could be used instead of a galvanometer. Typically, imaging system 100 obtains an image of a 2-dimensional area by scanning the laser beam in one dimension while moving the sample in an orthogonal direction.

Optimally, sample 118 is positioned such that the plane of interest (e.g. the surface to which labeled target molecules are bound) is located in the plane where the laser light is focused. Light remitted by sample 118 is collected by lens 116, reflected by mirror 114, and transmitted through lenses 112 and 111. Remitted light may consist of fluorescence, phosphorescence, specular reflection, diffuse reflection, Raman scattering, etc. Remitted light having a wavelength greater than 555 nm passes through dichroic beamsplitter 108 and is focused by lens 134 onto pinhole 136. Remitted light having a wavelength between 515 and 555 nm is reflected by beamsplitter 108, passes through dichroic beamsplitter 106, and is focused by a lens 120 onto a pinhole 122. The light that is transmitted through pinholes 136 and 122 impinges upon filters 138 and 124, respectively; the light that passes through these filters impinges upon photodetectors 140 and 126, respectively. Filter 138 transmits light having wavelengths between 555 and 607 nm, and filter 124 transmits light having wavelengths between 515 and 545 nm. Remitted light having wavelengths less that 515 nm is reflected by beamsplitters 108 and 106 and partially reflected by beamsplitter 104; the light reflected by beamsplitter 104 is focused by a lens 132 onto a pinhole 128. The light that is transmitted through pinhole 128 impinges upon a photodetector 130.

Pinholes 136, 122, and 128 are typically confocal pinholes. Specifically, remitted light that originates from the location on sample 118 where the laser beam is focused is maximally transmitted through the pinholes, while light that originates from other locations is not. Lenses 134, 120, and 132 preferably have focal lengths of 50 mm. Pinholes 136 and 122 preferably have diameters of 100 microns; pinhole 128 preferably has a diameter of 50 microns. Other lens focal lengths and pinhole diameters can be used, but system performance (confocality, sensitivity to misalignment, etc.) may be affected.

If lens 116 is not fully corrected for lateral color, the remitted light that is focused onto pinholes 136 and 122 might move laterally (across the plane of the pinhole) as mirror 114 is scanned. In this case it might be advantageous to use pinholes that are elliptical or rectangular rather than round, or to use slits instead of pinholes. For example, lens 116 in the present scanner has about 3 microns of lateral color at the edges of the scan field; consequently, the remitted light can move laterally by about 40 microns across the pinholes. Reasonable sizes for pinholes 136 and 122 in this case might be approximately 75 microns by 125 microns.

Photodetectors 140 and 126 are typically photomultipliers and are typically intended for the detection of relatively weak signals such as fluorescence. Various light detectors may be used, including photodiodes, avalanche photodiodes, phototransistors, vacuum photodiodes, photomultiplier tubes, and other light detectors.

Typically, photodetector 130 is used to aid in focusing the sample prior to scanning or while it is being scanned. The amount of reflected laser light reaching photodetector 130 is a maximum when the laser beam is focused onto the surface of sample 118. Focusing can be done either manually, or by a motorized translation stage under computer control. Frequently, sample 118 is a glass slide mounted in a liquid-filled flow cell (see FIG. 2) and the surface of interest is the second surface of the glass, i.e. the glass-liquid interface. Typically the reflection from this surface is much weaker than the reflection from the first surface of the glass, i.e. the glass-air interface, but the system is sufficiently confocal that the reflection peaks from the 2 surfaces are well separated.

The system described above is particularly useful in the detection of fluorescence from targets that are labeled with dyes such as fluorescein and phycoerythrin. Other dyes (rhodamines, carbocyanines, etc.) can be used, but laser 102, beamsplitters 108 and 106, and filters 138 and 124 may need to be altered depending on the dyes' absorption and emission spectra.

In some cases, target molecules may be labeled with particles or very large molecules that scatter laser light but do not fluoresce. In these cases, it may be desirable to detect diffusely scattered light but not specularly reflected laser light. An annular aperture can be placed between beamsplitter 104 and lens 132. If the inner diameter of the annulus is selected properly, this aperture will block specularly reflected laser light while transmitting diffusely scattered laser light, which can then be detected by photodetector 130.

Objective lens 116 was designed to meet a number of specifications, and may be obtained from, e.g., Special Optics, Part No. 55-S30-15 (Wharton, N.J.). The objective lens is usable with a galvanometer (or resonant scanner, rotating polygon, etc.), i.e. with an entrance pupil that is external to the lens and is located at or near the galvanometer mirror's pivot location. The lens is also capable of focusing a TEM00-mode laser beam having a wavelength of 488 nm to a spot having a diameter no greater than 3 microns at the $1/e^2$ intensity points, and should be capable of doing this at any point within a flat field having a diameter no less than 14 mm.

Objective lens 116 is within 2 degrees of telecentric, i.e. the transmitted laser beam should be parallel to the optical axis of the lens to within 2 degrees. (If the lens is not telecentric or nearly so, specularly reflected light from near the edges of the field might miss the lens and therefore not be detected.) In addition, lens 116 was designed so that the F/number would be no greater than f/2, i.e. numerical aperture no less than 0.25, with no vignetting even at the edges of the field. (F/number is a measure of the lens's light-gathering ability and is important if the lens is to be used for the detection of weak signals). Objective lens 116 is capable of focusing a polychromatic beam, having wavelengths between 488 and 600 nm and filling the entrance pupil, to a spot having a diameter no greater than 10 microns, and is capable of doing this at any point within a flat field having a diameter no less than 14 mm.

Objective lens 116 preferably has a focal length of about 30 mm. A lens having a different focal length, but still meeting the above specifications could be readily designed and would be acceptable for the purposes described herein. Lens 116 can focus a 488 nm laser beam to a diffraction-limited spot when the ratio of input beam diameter to lens focal length is less than approximately 0.21, e.g. it can focus a 6.2 mm diameter beam to a 3 micron diameter spot. If a larger focal spot is desired, the input beam diameter can be made smaller, e.g. by changing the ratio of the focal lengths of lenses 111 and 112 or by demagnifying the beam between laser 102 and beamsplitter 104.

Lens 116 was designed to be able to image a 14 mm field with 3 micron resolution and 0.25 numerical aperture; however, the design can easily be scaled up, e.g. to image a 28 mm field with 6 micron resolution and 0.25 numerical aperture (or potentially, to image a 280 mm field with 60 micron resolution and 0.25 numerical aperture, although the lens would be extremely large and costly). This scale-up involves merely multiplying the thicknesses, diameters, and radii of curvature of all of the elements of lens 116 by a constant. Similarly, the entire scanner can be scaled up for imaging of larger areas by multiplying all of the lens diameters and focal lengths, pinhole diameters, and mirror diameters by the same factor.

B. Data Acquisition

Figure 3:
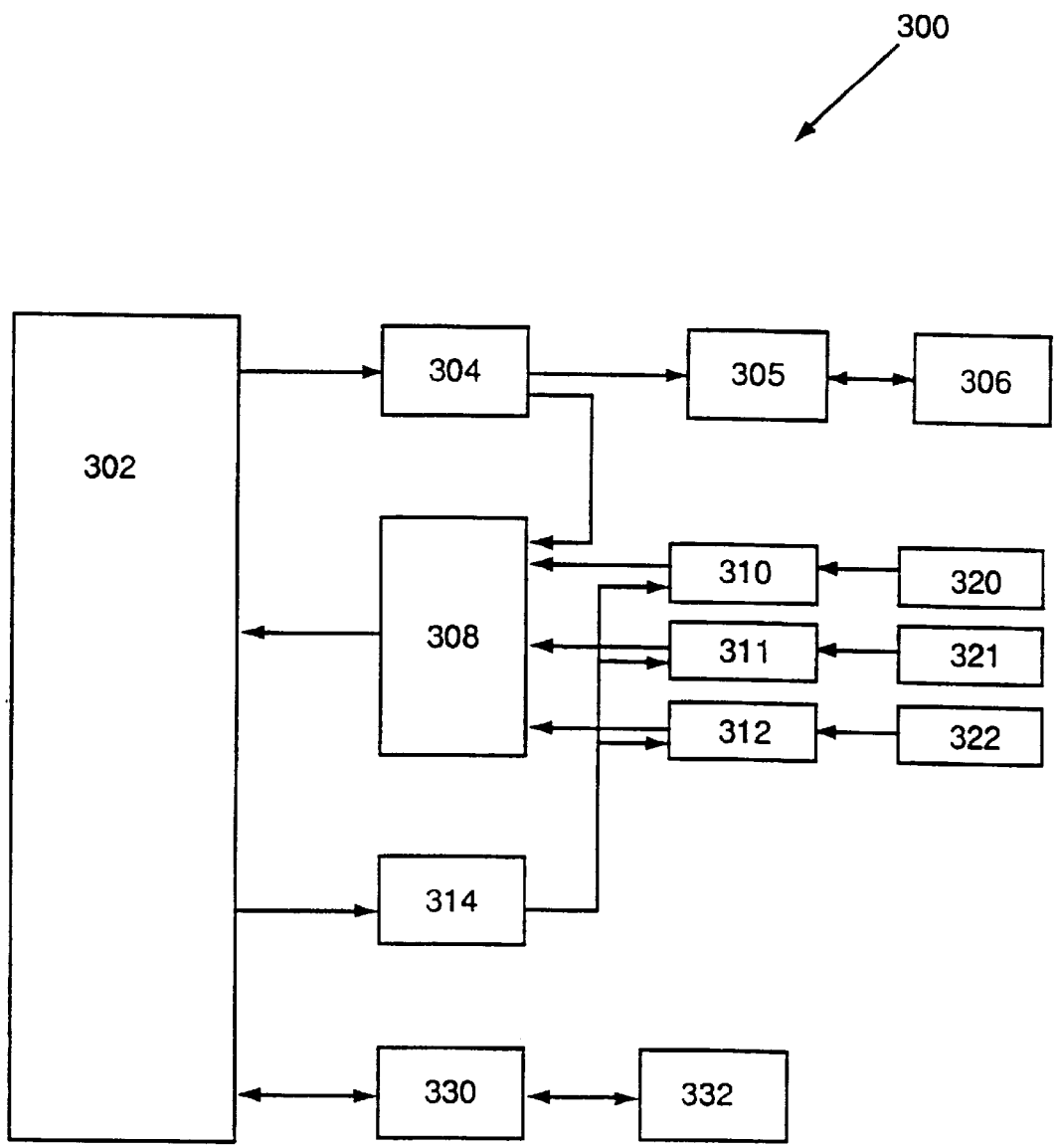
FIG. 3 is a schematic illustration of a computer based system for controlling and recording data from a scanning system according to the present invention.

As shown in FIG. 3, imaging system 300 includes a galvanometer 306 (to which a mirror 114 is attached) and a galvanometer driver board 305, which can be obtained from General Scanning Inc. (Watertown, Mass.). Galvanometer 306 is a model m2T. Other suitable galvanometers and driver boards are available, e.g. from Cambridge Technology Inc. (Watertown, Mass.). The input to driver board 305 is a voltage waveform from arbitrary waveform generator 304 (Keithley Metrabyte model PCIP-AWFG, Taunton, Mass.), which is installed in an ISA slot in computer 302. Circuitry on board 305 attempts at every instant to force galvanometer 306 to whatever angular position is commanded by waveform generator 304 (the desired angular position is linearly related to the waveform voltage). Waveform generator 304, after being programmed, can generate a waveform indefinitely without further intervention by computer 302. The waveform used is typically a sawtooth wave: e.g. if the waveform period is 33.3 msec, the voltage ramps up linearly for 25 msec, during which time data are acquired as the laser beam sweeps across the field; during the next 8.3 msec the voltage returns to its initial value and the laser beam retraces. Other waveforms such as sine waves or symmetric triangle waves could be used. Various methods of waveform generation that do not require the PCIP-AWFG waveform generator are known.

Currents from photomultipliers 320 and 321 and from photodiode 322 are converted to voltages by either transimpedance amplifiers or load resistors, optionally followed by voltage amplifiers. Simple op-amp circuits for this purpose are well known. The voltages are then low-pass filtered by filters 310, 311, and 312, e.g., programmable 4-pole Bessel filters (Frequency Devices model 824L8L-6, Haverhill, Mass.). Filter cutoff frequencies are digitally programmable in 400-Hz steps from 400 Hz to 102.4 kHz and are set by digital input-output board 314 (Computer Boards Inc. model CIO-DIO24, Mansfield, Mass.) installed in computer 302. Similar digital I/O boards are available from several other manufacturers. Filter cutoff frequencies are set by software so that each filter's output rise time in response to a step input is approximately equal to the time between A/D conversions. For example, if A/D conversions are 6 microseconds apart, the cutoff frequencies are set to 66 kHz. A variety of other types of filters (filters with more or fewer poles of different transfer functions (e.g. Butterworth), fixed-frequency filters, or simple RC filters) could be used instead.

Filter outputs are digitized by a 12-bit, 330 kHz analog-to-digital converter on data acquisition board 308 (Computer Boards Inc. model CIO-DAS 16/330). Similar data acquisition boards are available from several other manufacturers. Digitized data are displayed by computer 302, typically in the form of a gray-scale image, and are written to the computer's hard disk for subsequent data analysis. If the internal clock on data acquisition board 308 is used to trigger A/D conversions, the images obtained may be slightly distorted. A/D conversions that are equally far apart in time are not equally far apart in space, i.e., the velocity of the laser beam across sample 118 is not exactly constant, partly because lens 116 is not an ideal f-theta lens, and partly because of non-ideal behavior by driver board 305 and galvanometer 306. Therefore, A/D conversions are preferably triggered by waveform generator 304, which has digital output channels in addition to its analog output channel. When waveform generator 304 is appropriately programmed and its digital output pulses are appropriately spaced, image distortion can be eliminated.

Typically 4096 A/D conversions are performed per scan line, and if the user wants fewer than 4096 pixels/line the A/D conversions are binned by software in groups of 2 or more. For example, if the length of a scan line is 14 mm, the laser beam moves 3.4 microns between one A/D conversion and the next; and if, for example, the user chooses a pixel size of 13.6 microns, software adds the numbers from 4 A/D conversions for each pixel. One version of the software allows 8192 A/D conversions per scan line. The utility of doing more A/D conversions per line diminishes as the pixel size becomes less than the laser spot size.

Translation stages 332 (typically a 2-axis or 3-axis set of stages) are controlled by indexer 330. Two axes of translation are usually used: a scan axis (parallel to the plane of the sample and perpendicular to the direction of motion of the laser spot), and a focus axis (parallel to the optical axis of lens 116). A third axis orthogonal to the other two may also be desirable. Computer 302 sends commands to indexer 330, and receives information about translation-stage status from indexer 330, e.g., using an RS-232 interface. An indexer that communicates with computer 302 using another interface, such as a GPIB or ISA interface, could be used instead. Translation stage speed is set such that the distance that sample 118 moves per scan line is equal to the desired pixel size.

Software allows the user to control various scan parameters, including the size of the area to be scanned, the pixel size, the scan speed, and which output or outputs to digitize (either of the photomultiplier outputs, or the photodiode output, or a combination thereof). Default parameters are 14 mm×14 mm scan area, 10.2 micron pixel size, and scan speed of 30 lines/second. With these parameters, an image contains 1365×1365 pixels and can be acquired in about 45 seconds. These parameters are usually suitable for users who need to image 12.8 mm×12.8 mm oligonucleotide arrays having features that are approximately 100 $\mu$m×100 $\mu$m. Other scan parameters are suitable in other circumstances. The source code for this software is enclosed in Appendix A, of which is hereby incorporated herein by reference for all purposes.

For example, if the features are 400 $\mu$m×400 $\mu$m the user might choose a pixel size of 27.2 microns. In this case an image of a 14 mm×14 mm area contains 512×512 pixels and can be obtained in about 17 seconds. On the other hand, if the features are 30 $\mu$m×30 $\mu$m, the user might choose a pixel size of 3.4 microns. In this case an image of a 14 mm×14 mm area contains 4096×4096 pixels and can be acquired in about 2 minutes and 16 seconds. If an image with adequate signal-to-noise ratio is not obtained at a scan speed of 30 lines/second, the user might choose to reduce the scan speed, for example to 7.5 lines/second (quadrupling the scan time approximately quadruples the number of photons detected per pixel, and therefore in many cases approximately doubles the signal-to-noise ratio).

Scanned areas can vary from the 14 mm×14 mm dimensions described above, and need not be square. For example, software options can allow the user to reduce the length of a scan line, e.g., to as little as 4 mm or smaller if a user so desired, with a pixel size as small as 1 micron, and to set the number of lines per scan independently of the other scan parameters. In the galvanometer-scanned direction, a single scan can not cover a region that is larger than the field of view of lens 116, e.g., 14 mm. However, the system may cover a region that is several inches wide in the orthogonal direction (limited only by the length of travel of the translation stage). Other software options allow users automatically to scan a chip several times, with any desired time interval between scans (useful for certain kinetics experiments), and automatically to scan several different chips on a wafer (useful for wafer inspection prior to dicing and packaging). Another option allows users to choose between 2 different output file formats: one format which saves "raw" data, with 2 bytes per pixel; and a space-saving format which saves "scaled" data, with one byte per pixel. A scaled data value is directly proportional to the square root of the raw data value. A lookup table for converting from scaled data back to raw data is stored in the file's header.

C. System for Holding a Sample Within a Flow Cell

Figure 2:
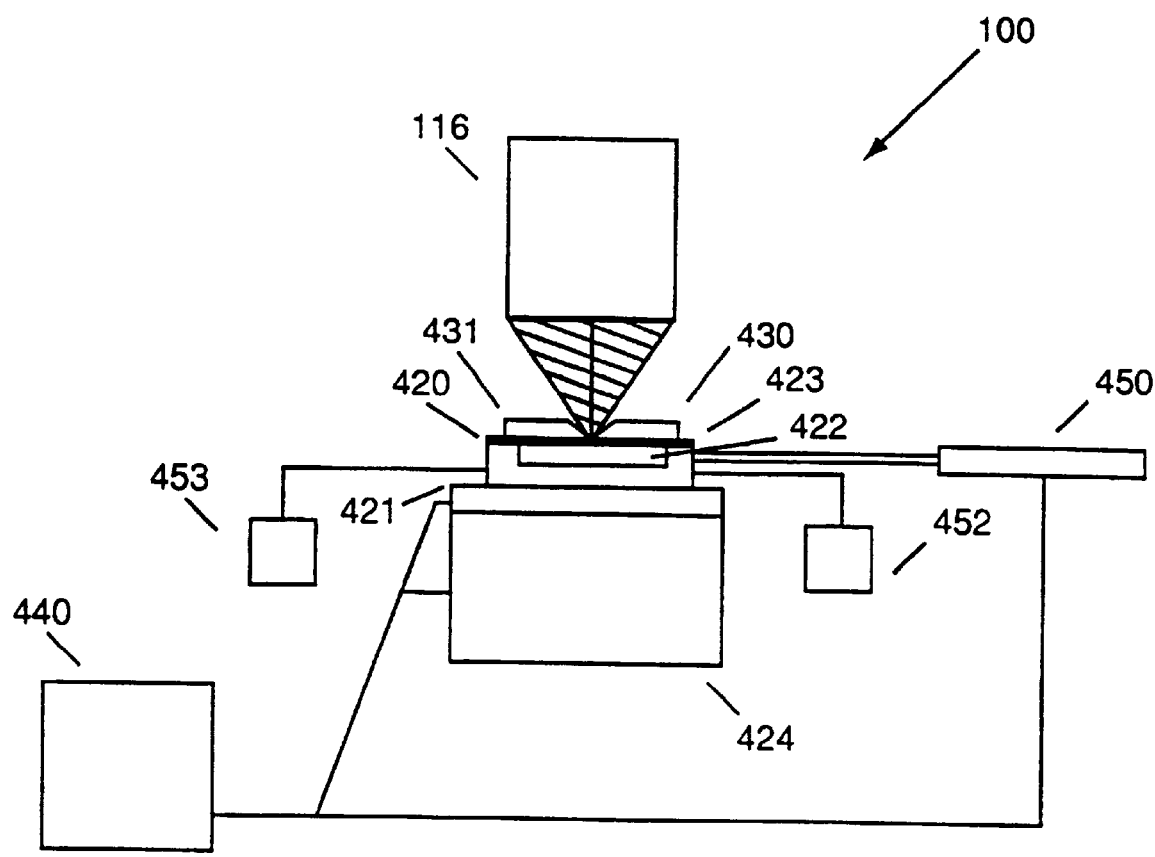
FIG. 2 illustrates one embodiment of a scanning system that includes a flow cell on which a substrate is mounted.

Referring to FIG. 2, a system and method for holding sample 118 within a flow cell will now be described. It should be clearly understood that the present invention is not limited to a flow cell. For example, the sample 118 may be part of a packaged chip, such as a diced chip glued into a disposable plastic package. A more complete description of a packaged chip can be found in commonly assigned, co-pending applications Ser. Nos. 08/485,452, filed Jun. 7, 1995 now U.S. Pat. No. 5,945,334, the complete disclosures of which are incorporated herein by reference for all purposes.

As shown, imaging system 100 further includes a body 422 for holding a support 430 containing the sample on a surface 431. In some embodiments, the support may be a microscope slide or any surface which is adequate to hold the sample. The body 422, depending on the application, may be a flow cell having a cavity 423. The flow cell, for example, may be employed to detect reactions between targets and probes. In some embodiments, the bottom of the cavity may comprise a light absorptive material so as to minimize the scattering of incident light.

In embodiments utilizing the flow cell, surface 431 is mated to body 422 and serves to seal cavity 423. The flow cell and the substrate may be mated for sealing with one or more gaskets. In one embodiment, the substrate is mated to the body by vacuum pressure generated by a pump 452. Optionally, the flow cell is provided with two concentric gaskets and the intervening space is held at a vacuum to ensure mating of the substrate to the gaskets. Alternatively, the substrate may be attached by using screws, clips, or other mounting techniques.

When mated to the flow cell, the cavity encompasses the sample. The cavity includes an inlet port 421 and an outlet port 420. A fluid, which in some embodiments contains fluorescently labeled targets, is introduced into the cavity through inlet port 421. A pump 453, which may be a model No. B-120-S made by Eldex Laboratories, circulates fluids into the cavity via inlet 421 port and out through outlet port 420 for recirculation or disposal. Alternatively, a syringe, gas pressure, or other fluid transfer device may be used to flow fluids into and through the cavity.

Optionally, pump 453 may be replaced by an agitation system that agitates and circulates fluids through the cavity. Agitating the fluids shortens the incubation period between the probes and targets. This can be best explained in terms of kinetics. A thin layer, known as the depletion layer, is located above the probe sample. Since targets migrate to the surface and bind with the probe sequences, this layer is essentially devoid of targets. However, additional targets are inhibited from flowing into the depletion layer due to finite diffusion coefficients. As a result, incubation period is significantly increased. By using the agitation system to dissolve the depletion layer, additional targets are presented at the surface for binding. Ultrasonic radiation and/or heat, shaking the holder, magnetic beads, or other agitating technique may also be employed.

In some embodiments, the flow cell is provided with a temperature controller 450 for maintaining the flow cell at a desired temperature. Since probe/target interaction is sensitive to temperature, the ability to control it within the flow cell permits hybridization to be conducted under optimal temperature. The temperature controller 450 may include a circulating bath, a refrigerated air circulating device, resistance heater, peltier device (thermoelectric cooler), or other temperature controller may be implemented.

As previously mentioned, the flow cell is oriented to maintain the substrate perpendicular to the optical axis of the collection optics. According to one embodiment, flow cell 422 may mounted to a translation stage 424 for moving the flow cell in an orthogonal direction relative to the optical path. The flow cell may be mated to the translation stage by vacuum pressure generated by pump 452. Alternatively, screws, clips or other mounting techniques may be employed to mate the flow cell to the translation stage.

IV. Detailed Description of an Alternative Embodiment of the Imaging System.

Figure 4:
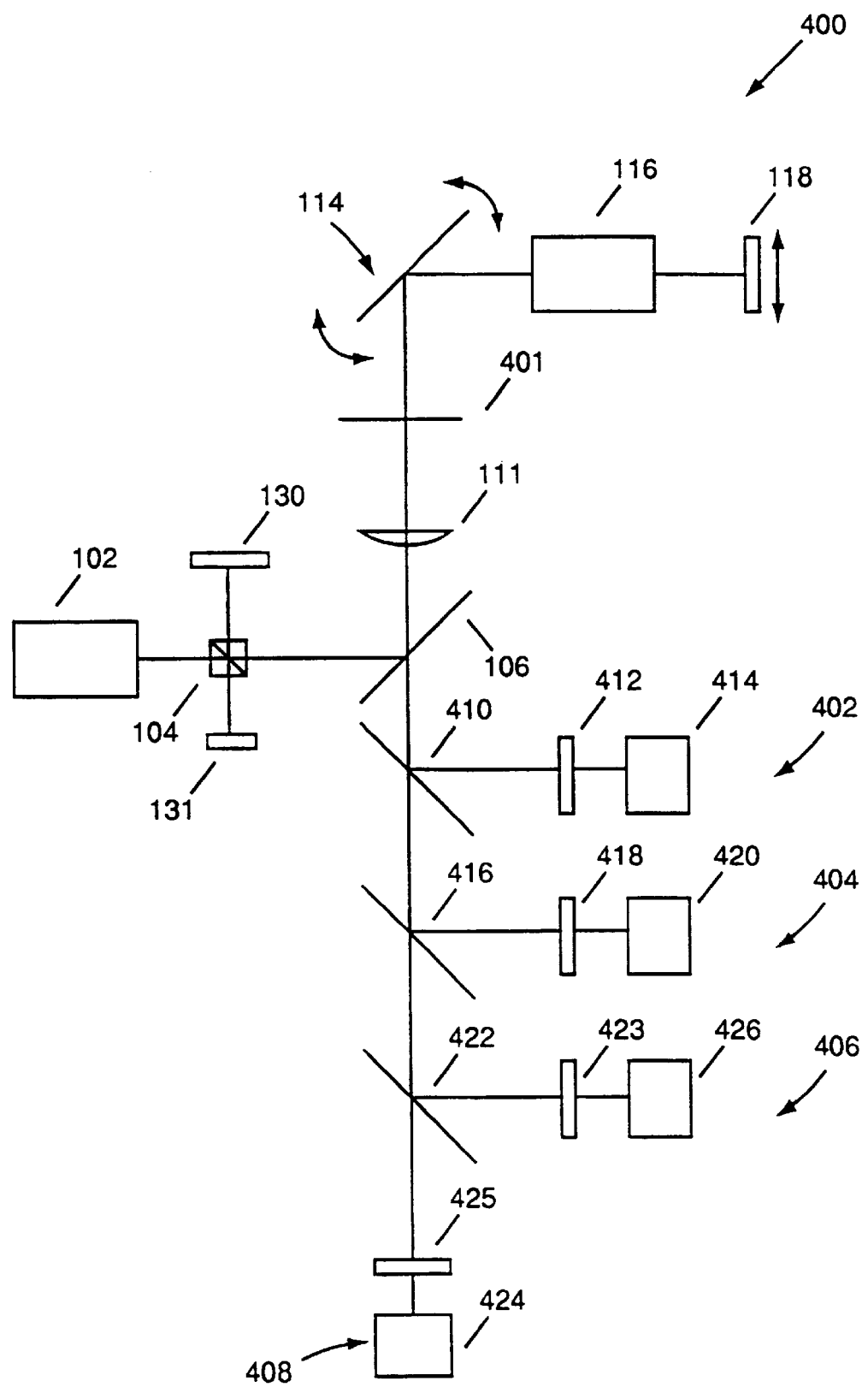
FIG. 4 is a schematic illustration of an alternate embodiment of a scanning system according to the present invention.

An optical block diagram of a second embodiment of imaging system 400 is shown in FIG. 4. As depicted, imaging system 400 comprises components which are common to the system described in FIG. 1. In this scanner, lens 116 is intended for use at a finite rather than an infinite conjugate ratio, and therefore lens 112 is omitted. This scanner uses only a single pinhole 401, and all of the remitted light passes through this pinhole 401 before being separated by the various dichroic beamsplitters. This scanner has 2 additional dichroic beamsplitters, spectral filters, and photomultipliers, and therefore can be used for 4-channel rather than merely 2-channel fluorescent scanning.

As discussed above in the previous embodiment, a beam of excitation radiation, e.g., 488 nm light, from a laser 102 is partially reflected and partially transmitted by a beamsplitter 104. The reflected portion of the beam impinges upon a photodetector 131 (optional), which is typically a photodiode used as a laser power monitor. The portion of the beam that is transmitted through beamsplitter 104 is reflected by dichroic beamsplitter 106 and transmitted through lens 111, focused onto pinhole 401, and expanded to the desired diameter at the entrance pupil lens 116.

The beam of excitation radiation is focused by lens 116 and scanned across the sample 118 by galvanometer mirror 114, as discussed above. Light remitted by sample 118 is collected by lens 116, reflected by mirror 114, and focused onto confocal pinhole 401. Light that is transmitted through pinhole 401 is collimated by lens 111. Remitted light having wavelengths less that 515 nm is reflected by beamsplitter 106 and partially reflected by beamsplitter 104; the light reflected by beamsplitter 104 impinges upon a photodetector 130. Remitted light having a wavelength above 515 passes through beamsplitter 106 and is sent to one of the four channels 402, 404, 406, 408 depending on its wavelength. For example, imaging system 300 may be constructed such that remitted light having a wavelength between 515 and 545 is reflected by dichroic beamsplitter 410, and passes through a filter 412 onto photodetector 414. Remitted light having a wavelength between 545 and 570 nm, for example, may be reflected by dichroic beamsplitter 416, where it passes through filter 418 and onto photodetector 420. Similarly, beamsplitter 422 is constructed to reflect remitted light having wavelengths between 570 and 595 nm through filter 423 onto photodetector 426. Remitted light having wavelengths greater than 595 nm are transmitted through beamsplitter 422, to pass through filter 425 onto photodetector 424.

The present invention is further illustrated by the following example. This example is merely to illustrate aspects of the present invention and is not intended as limitations of this invention.

EXAMPLE

A tiling array was designed for the entire human mitochondrial genome. See M. Chee et al., "Accessing genetic information with high-density DNA arrays", *Science* vol. 274, pgs. 610–614 (1996). The array contained 134,688 different probe sequences, each occupying a separate 35 μm feature. The overall array dimensions were 1.28 cm×1.28 cm. Using long range PCR and RNA polymerase promoter tagged primers, a 16.3 kb fragment of mtDNA was amplified directly from genomic DNA samples. Labeled 16.3 kb RNA targets were prepared by in vitro transcription from the PCR amplicons and hybridized to the array.

Figure 5:
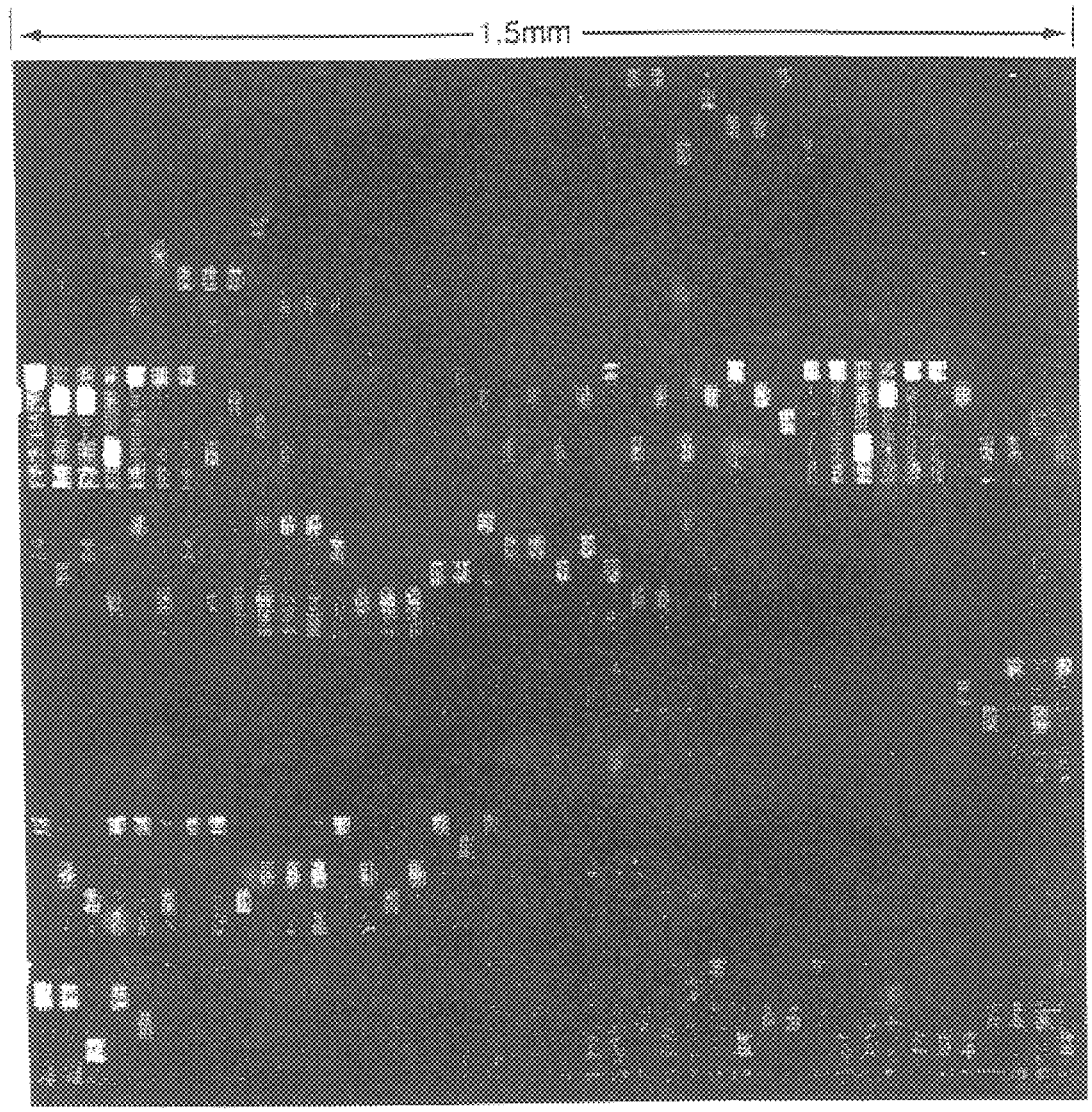
FIG. 5 is an enlarged view of a scanned image generated using a scanning system of the present invention.

A scanning system as described above was used to scan the array and a 4096×4096 pixel image was obtained, each pixel representing 3.4 μm. The entire array was scanned in under three minutes. A close-up view of a scanned image of this array is shown in FIG. 5. The scanned image shown covers a 1.5 mm×1.5 mm segment of a 14 mm×14 mm image of a 12.8 mm×12.8 mm array.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A system for detecting marked regions on a surface of a substrate, the system comprising:

an excitation radiation source;

a focusing system for focusing radiation from said excitation radiation source onto a selected region of said surface of said substrate, said focusing system including an objective lens having a ratio of scanning field diameter to focused spot diameter of greater than about 2000, and a numerical aperture greater than about 0.2;

a reciprocating radiation direction system comprising a mirror selected from the group consisting of a galvanometric mirror, angularly oscillating mirror or a rotating polyhedral mirror for scanning said focused excitation radiation across said surface of said substrate at a rate of at least 20 image lines/second;

a detector for detecting an emission from said surface of said substrate in response to said excitation radiation, wherein said objective lens receives said emission and transmits the emission to the detector; and a data acquisition system for recording an amount of said emission detected as a function of a position on said surface of said substrate from which said emission was emitted.

2. The system of claim 1, wherein said focusing system has a ratio of scanning field diameter to focused spot diameter of greater than 3000.

3. The system of claim 1, wherein said focusing system has a ratio of scanning field diameter to focused spot diameter of greater than 4000.

4. The system of claim 1, wherein said focusing system focuses said excitation radiation in a spot having a diameter of less than about 10 μm.

5. The system of claim 1, wherein said focusing system focuses said excitation radiation on said surface of said substrate in a spot having a diameter of less than about 5 μm.

6. The system of claim 1, wherein said focusing system focuses said excitation radiation on said surface of said substrate in a spot having a diameter of about 3 μm.

7. The system of claim 1, wherein said objective lens has a scanning field diameter is greater than about 10 mm.

8. The system of claim 1, wherein said scanning field diameter is about 14 mm.

9. The system of claim 1, wherein said numerical aperture is greater than about 0.25.

10. The system of claim 1, wherein said focusing system is achromatic.

11. The system of claim 1, wherein said radiation direction system is capable of scanning a spot across the substrate at a rate of at least 10 image lines/second.

12. The system of claim 1, wherein said radiation direction system is capable of scanning a spot across the substrate at a rate of at least 30 image lines/second.

13. The system of claim 1, further comprising a translation stage upon which said substrate is mounted, said translation stage being moveable in at least one dimension perpendicular to an optical axis of said objective lens.

14. The system of claim 1, further comprising an autofocus system for placing said surface of said substrate in a focal plane of said focusing system.

15. The system of claim 1, further comprising a translation stage upon which said substrate is mounted, said translation stage being moveable in at least one dimension parallel to an optical axis of said focusing system and at least one dimension perpendicular to said optical axis of said focusing system.

16. The system of claim 1 further comprising a collection system comprising:
    collection optics for collecting fluorescent radiation emitted from said surface of said substrate and for collecting said excitation radiation reflected from said surface of said substrate;
    separation optics for separating said fluorescent radiation from said excitation radiation and focusing said fluorescent radiation through a confocal pinhole; and
    a recorder responsive to said fluorescent radiation, for recording an amount of said fluorescence focused through said confocal pinhole.

17. The system of claim 1, wherein said surface of said substrate comprises a plurality of distinct polymer sequences in different known locations on said surface.

18. The system of claim 17, wherein each of said different polymer sequences is contained in a feature having at least one of a width or length dimension of less than about 50 $\mu$m.

19. The system of claim 1 further comprising a processor for processing and storing a signal so as to generate a 2-dimensional image of said substrate.

20. The system of claim 1 further comprising a body for immobilizing said substrate, the substrate having at least a first surface with a sample thereon, the body comprising:
    a mounting surface;
    a cavity in said mounting surface, said first surface mated to said mounting surface for sealing said cavity, said sample being in fluid communication with said cavity, said cavity having a bottom surface comprising a light absorptive material;
    an inlet and an outlet being in communication with said cavity such that fluid flowing into said cavity for contacting said sample flows through said inlet and fluid flowing out of said cavity flows through said outlet; and
    a temperature controller for controlling the temperature in said cavity.

21. The system of claim 20 wherein said temperature controller comprises a thermoelectric cooler.

22. A system for detecting marked regions on a surface of a substrate, the system comprising:
    an excitation radiation source;
    first focusing optics for focusing said excitation radiation on said surface of said substrate in a spot having a diameter no greater than 5 $\mu$m, said focusing optics including an objective lens having a ratio of scanning field diameter to focussed spot diameter of greater than about 2000;
    a reciprocating radiation direction system comprising a mirror selected from the group consisting of a galvanometric mirror, angularly oscillating mirror or rotational polyhedral mirror for scanning said spot linearly across said surface of said substrate at a rate of at least 20 image lines/second said spot having a travel distance of at least 10 mm;
    an optical train for separating emissions from said surface of said substrate from excitation radiation reflected from said surface of said substrate, said optical train including said objective lens, said objective lens receiving both said reflected excitation radiation and said emissions therethrough; and
    an autofocus system for automatically placing said surface of said substrate in a focal plane of said first focusing optics.

23. The system of claim 22, wherein said optical train includes a dichroic beam splitter for separating fluorescence emitted from said surface of said substrate from excitation radiation reflected from said surface of said substrate.

24. The system of claim 22, wherein said autofocus system comprises:
    second focusing optics for focusing said excitation radiation reflected from said surface of said substrate through a confocal pinhole onto a photodiode; and
    a translation stage upon which a substrate is mounted, said stage being capable of moving in a direction parallel with an optical axis of said first focusing optics for moving said substrate into a focal plane of said first focusing optics.

25. The system of claim 22 further comprising
    a detector for detecting an emission from said surface of said substrate in response to said excitation radiation, and a data acquisition system for recording an amount of said emission detected as a function of a position on said surface of said substrate from which said emission was emitted.

26. A method of scanning a polymer array having a plurality of different polymer sequences, each of said different polymer sequences being immobilized on a surface of a substrate in a different known location, to identify which polymer sequence on said array is bound by a target molecule, the method comprising:
    focusing an excitation radiation source upon said surface of said substrate with an objective lens having a ratio of scanning field diameter to focussed spot diameter of greater than about 2000;
    scanning said excitation radiation across said surface of said substrate at a speed of at least about 20 image lines/second said scanning comprising using a mirror selected from the group consisting of a galvanometric mirrors, angularly oscillating mirror or rotating polyhedral mirror to direct said excitation radiation through said objective lens and across said substrate;
    collecting emissions from said surface of said substrate in response to said excitation radiation with said objective lens;

collecting excitation radiation reflected from said substrate, thereby focussing said emissions; and recording said emissions as a function of a position on said surface of said substrate, said position indicating the polymer sequence on said array is bound by a target molecule.

27. The method of claim 26, wherein said polymer array comprises a plurality of different oligonucleotide sequences immobilized on said surface of said substrate in different known locations.

28. The method of claim 26 further comprising focusing the excitation radiation source to a spot having a diameter of about 3 µm and scanning the spot in linear direction across the substrate for at least 14 mm.

29. The method of claim 26 further comprising the steps of:

immobilizing said substrate on a body;

exciting said surface on said substrate with an excitation radiation having a first wavelength from an electromagnetic radiation source, said excitation radiation being focussed on said substrate by an objective lens having a ratio of scanning diameter to focussed spot diameter of greater than about 2000; exciting performed at a rate of at least 20 image lines/second;

detecting response radiation having a second wavelength, said response radiation being generated in response to said excitation radiation, said response radiation representing an image of a first plurality of regions, said response radiation being focussed through said objective lens;

exciting a subsequent plurality of regions on said sample;

processing and storing said response radiation to generate a 2-dimensional image of said sample;

separating excitation radiation reflected from said substrate from said response radiation; and detecting said reflected excitation radiation, thereby autofocusing said sample in a focal plane of said excitation radiation.

30. The method as recited in claim 29 wherein said body comprises a mounting surface having a cavity thereon, said substrate being immobilized on said mounting surface such that said surface is in fluid communication with said reaction chamber, a reaction chamber comprising a inlet and a outlet for flowing fluids into and through said reaction chamber.

31. The method as recited in claim 30 wherein said body further comprises a temperature controller for controlling the temperature in said cavity.

32. The method as recited in claim 26 wherein said excitation radiation is scanned across said surface of said substrate at a speed of at least about 10 image lines/second.

33. The method as recited in claim 26 wherein said excitation radiation is scanned across said surface of said substrate at a speed of at least about 30 image lines/second.

* * * * *